United States Patent [19]

Zhuang et al.

[11] Patent Number: 6,015,918

[45] Date of Patent: Jan. 18, 2000

[54] ALLYL-DERIVED PRECURSOR AND SYNTHESIS METHOD

[75] Inventors: Wei-Wei Zhuang; Tue Nguyen; Greg Michael Stecker, all of Vancouver, Wash.; David Russell Evans, Beaverton, Oreg.; Sheng Teng Hsu, Camas, Wash.

[73] Assignee: Sharp Laboratories of America, Inc., Camas, Wash.

[21] Appl. No.: 09/281,731

[22] Filed: Mar. 30, 1999

Related U.S. Application Data

[60] Provisional application No. 60/107,892, Nov. 10, 1998.

[51] Int. Cl.$^7$ .................................. C07F 1/08; C07F 1/10
[52] U.S. Cl. .......................... 556/117; 556/136; 427/587; 427/248.1
[58] Field of Search ...................... 556/117, 136

[56] References Cited

U.S. PATENT DOCUMENTS

| | | | |
|---|---|---|---|
| 4,385,005 | 5/1983 | Doyle | 260/464 |
| 4,425,281 | 1/1984 | Doyle | 260/430 |
| 5,085,731 | 2/1992 | Norman et al. | 156/646 |
| 5,096,737 | 3/1992 | Baum et al. | 427/38 |

OTHER PUBLICATIONS

Article entitled, "Alkene and Carbon Monoxide Derivatives of Copper (I) and Silver (I) B–Diketonates" by G. Doyle, K.A. Eriksen, and D. Van Engen, Organometallics, 1985, 4, 830–835.

Article entitled, "Low Temperature Chemical Vapor Deposition of High–Purity Copper from an Organometallic Source" by David B. Beach, Franscoise K. LeGouses,and Chao–Kun Hu, Chem. Mater, 1990, 2, 216–219.

Article entitled, "Chemical Vapor Deposition of Copper from Copper (I) Trimethylphosphine Compounds" by M.J. Hampden–Smith, T.T. Kodas, M. Paffett, J.D. Farr, and H.–K. Shin, Chem. Mater, 1990, 2, 636–639.

Article entitled, "A Novel Copper Complex and CVD Precursor: (n$^2$–2–Butyne)copper(I) Hexafluoroacetylacetonate", by Thomas H. Baum and Carl E. Larson, Chem. Mater, 1992, 4, 365–369.

Article entitled, "Chemical Vapor Deposited Copper from Alkyne Stabilized Copper (I) Hexafluoroacetylacetonate Complexes", by Thomas H. Baum and Carl E. Larson, J. Electrochem. Soc., vol. 140, Jan. 1, 1993, 154–158.

Article entitled, "Chemical Vapor Deposition of Copper Thin Films with (hexafluoroacetylacetonate)Cu(allyltrimethylsilane)", by Man–Young Park, Jong–Hoon Son, and Shi–Woo Rhee, Electrochemical and Solid–State Letters, 1 (1), 32–33, (1998).

Abstract entitled, "MOCVD of Copper from the Solution of New and Liquid Precursor (hfac)Cu(1–pentene)", by H.–K. Shin, Y.–H. Cho, D.–J. Yoo, H.–J. Shin, and E.–S. Lee, Materials Research Soc. Symp. Proc., vol. 514, 301.

Article entitled, "Hexafluoroacetylacetonate Cu Vinylcyclohexane as a Liquid Precursor for Low Temperature Chemical Vapor Deposition of Copper Thin Films", by Sang–Woo Kang, Man–Young Park, and Shi–Whoo Rhee, Electrochemical and Solid–State Letters, 2 (1), 22–23. (1999).

Shin et al., Chemical Abstracts, vol. 126, No. 7, abstract No. 97083k, p. 1296, Feb. 17, 1997.

*Primary Examiner*—Porfirio Nazario-Gonzalez
*Attorney, Agent, or Firm*—Gerald Maliszewski; David C. Ripma

[57] ABSTRACT

A Cu(hfac) allyl-derived ligand precursor has been provided. The ligand includes group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene. Examples of the allyl-derived ligand precursors have proved to be stable at room temperatures, and sufficiently volatile at higher temperatures. Copper deposited with this precursor has low resistivity and high adhesive characteristics. A synthesis method has been provided which produces a high yield of the above-described precursors, including a Cu(hfac)(allyltrimethylsilane) precursor.

21 Claims, 4 Drawing Sheets

ALLYL-DERIVED PRECURSOR AND SYNTHESIS METHOD

This invention claims the benefit of a provisional application Ser. No. 60/107,892, filed Nov. 10, 1998, entitled "Improved Copper Precursor and Synthesis Method".

BACKGROUND AND SUMMARY OF THE INVENTION

This invention relates generally to integrated circuit processes and fabrication, and more particularly, to a precursor and synthesis method, having an allyl-derived ligand, which improves volatility, and which is capable of depositing copper at high deposition rates, low resistivity, and with good adhesion on selected integrated circuit surfaces.

The demand for progressively smaller, less expensive, and more powerful electronic products, in turn, fuels the need for smaller geometry integrated circuits (ICs) on larger substrates. It also creates a demand for a denser packaging of circuits onto IC substrates. The desire for smaller geometry IC circuits requires that the interconnections between components and dielectric layers be as small as possible. Therefore, research continues into reducing the width of via interconnects and connecting lines. The conductivity of the interconnects is reduced as the area of the interconnecting surfaces is reduced, and the resulting increase in interconnect resistivity has become an obstacle in IC design. Conductors having high resistivity create conduction paths with high impedance and large propagation delays. These problems result in unreliable signal timing, unreliable voltage levels, and lengthy signal delays between components in the IC. Propagation discontinuities also result from intersecting conduction surfaces that are poorly connected, or from the joining of conductors having highly different impedance characteristics.

There is a need for interconnects and vias to have both low resistivity, and the ability to withstand process environments of volatile ingredients. Aluminum and tungsten metals are often used in the production of integrated circuits for making interconnections or vias between electrically active areas. These metals are popular because they are easy to use in a production environment, unlike copper which requires special handling.

Copper (Cu) would appear to be a natural choice to replace aluminum in the effort to reduce the size of lines and vias in an electrical circuit. The conductivity of copper is approximately twice that of aluminum and over three times that of tungsten. As a result, the same current can be carried through a copper line having nearly half the width of an aluminum line.

The electromigration characteristics of copper are also much superior to those of aluminum. Aluminum is approximately ten times more susceptible than copper to degradation and breakage due to electromigration. As a result, a copper line, even one having a much smaller cross-section than an aluminum line, is better able to maintain electrical integrity.

There have been problems associated with the use of copper, however, in IC processing. Copper pollutes many of the materials used in IC processes and, therefore barriers are typically erected to prevent copper from migrating. Elements of copper migrating into these semiconductor regions can dramatically alter the conduction characteristics of associated transistors. Another problem with the use of copper is the relatively high temperature needed to deposit it on, or removing it from, an IC surface. These high temperatures can damage associated IC structures and photoresist masks.

It is also a problem to deposit copper onto a substrate, or in a via hole, using the conventional processes for the deposition of aluminum when the geometries of the selected IC features are small. That is, new deposition processes have been developed for use with copper, instead of aluminum, in the lines and interconnects of an IC interlevel dielectric. It is impractical to sputter metal, either aluminum or copper, to fill small diameter vias, since the gap filling capability is poor. To deposit copper, first, a physical vapor deposition (PVD), and then, a chemical vapor deposition (CVD) technique, have been developed by the industry.

With the PVD technique, an IC surface is exposed to a copper vapor, and copper is caused to condense on the surfaces. The technique is not selective with regard to surfaces. When copper is to be deposited on a metallic surface, adjoining non-conductive surfaces must either be masked or etched clean in a subsequent process step. As mentioned earlier, photoresist masks and some other adjoining IC structures are potentially damaged at the high temperatures at which copper is processed. The CVD technique is an improvement over PVD because it is more selective as to which surfaces copper is deposited on. The CVD technique is selective because it is designed to rely on a chemical reaction between the metallic surface and the copper vapor to cause the deposition of copper on the metallic surface.

In a typical CVD process, copper is combined with a ligand, or organic compound, to help insure that the copper compound becomes volatile, and eventually decomposes, at consistent temperatures. That is, copper becomes an element in a compound that is vaporized into a gas, and later deposited as a solid when the gas decomposes. Selected surfaces of an integrated circuit, such as diffusion barrier material, are exposed to the copper gas, or precursor, in an elevated temperature environment. When the copper gas compound decomposes, copper is left behind on the selected surface. Several copper gas compounds are available for use with the CVD process. It is generally accepted that the configuration of the copper gas compound, at least partially, affects the ability of the copper to be deposited on to the selected surface.

Copper metal thin films have been prepared via chemical vapor deposition by using many different kinds of copper precursors. In 1990, D. B. Beach et al. *Chem. Mater.* (2) 216 (1990) obtained pure copper films via CVD by using ($\eta^5$-$C_5H_5$)Cu(PMe$_3$), and later, in 1992, H. K. Shin et al., *Chem. Mater.* (4) 788 (1992) declared the same results by using (hfac)Cu(PR$_3$)$_n$(R=methyl and ethyl and n=1 and 2). However, these copper precursors are solids, which can not be used in the liquid delivery system for copper thin film CVD processing. Furthermore, the copper films often contain contamination of carbon and phosphorus, which can not be used as interconnectors in microprocessors.

$Cu^{2+}$(hfac)$_2$, or copper (II) hexafluoroacetylacetonate, precursors have previously been used to apply CVD copper to IC substrates and surfaces. However, these $Cu^{2+}$ precursors are notable for leaving contaminates in the deposited copper, and for the relatively high temperatures that must be used to decompose the precursor into copper.

The studies of copper precursors conducted in the early of 1990's were concentrated on the evaluation of a series of copper(I) fluorinated β-diketonate complexes, which have been proven to be very promising sources for the use in the chemical vapor deposition of copper metal thin films. Copper(I) fluorinated β-diketonate complexes were first synthesized by Gerald Doyle, U.S. Pat. No. 4,385,005 (1983) and U.S. Pat. No. 4,425,281 (1984), in which he presented the synthesis method and their application in the separation of unsaturated organic hydrocarbons. In the U.S. Pat. No. 5,096,737 (1992), Thomas H. Baum, et at., claimed the application of these copper(I) fluorinated β-diketonate complexes as copper precursors for CVD copper thin film preparation. Copper thin films have been prepared via chemical vapor deposition using these precursors.

Among several liquid copper precursors, 1,5-dimethyl 1,5-cyclooctadiene copper(I) hexafluoroacetylacetonate mixed with 1,6-dimethyl 1,5-cyclooctadiene copper(I) hexafluoroacetylacetonate ((DMCOD)Cu(hfac)) and hexyne copper(I) hexafluoroacetylacetonate ((HYN)Cu(hfac)) were evaluated in detail. The copper thin films deposited using (DMCOD)Cu(hfac) have very good adhesion to metal or metal nitride substrates, but a high resistivity (2.5 $\mu\Omega$·cm) and a low deposition rate. (HYN)Cu(hfac) copper film has poor adhesion to a TiN substrate, and high resistivity (~2.1 $\mu\Omega$·cm). Another compound, butyne copper(I)(hfac), ((BUY)Cu(hfac)), gives a copper film with low resistivity (1.93 $\mu\Omega$ cm), but has poor adhesion and is relatively expensive. Also, the compound is a solid and, therefore, difficult to use in a liquid delivery system. The invention of copper(I)(hfac) stabilized with a series of trialkylvinylsilane (John A. T. Norman et al., U.S. Pat. No. 5,085,731 (1992)) improved the properties of copper thin films.

Copper films deposited using a liquid copper precursor, (hfac)Cu(TMVS), where TMVS=trimethylvinylsilane, have low resistivities and reasonably adhesion to substrates. This precursor is useful because it can be used at relatively low temperatures, approximately 200° C. This liquid copper precursor has been used for the preparation of copper metal thin films via CVD for some time, but there are still some drawbacks: stability, the adhesion of copper films, and cost for the trimethylvinylsilane stabilizer. Also, the precursor is not especially stable, and can have a relatively short shelf life if not refrigerated. Various ingredients have been added to (hfac)Cu(tmvs) to improve its adhesiveness, temperature stability, and the rate at which it can be deposited on an IC surface. U.S. Pat. No. 5,744,192, entitled "Method Of Using Water To Increase The Conductivity Of Copper Deposited With Cu(HFAC)TMVS", invented by Nguyen et al., discloses a precursor and method of improving the electrical conductivity of Cu deposited with (hfac)Cu(tmvs).

It is generally acknowledged in the industry that (hfac) Cu(tmvs) becomes unstable, and begins to decompose, above 35° C. Use of a (hfac)Cu(tmvs) precursor stored at this temperature leads to undesirable process results. The effectivity of (hfac)Cu(tmvs) stored at temperatures lower than 35° C. is also unpredictable. A "fresh" batch of precursor, or precursor stored at temperatures well below room temperature, is used to guarantee predictable processes.

A Cu precursor comprising a ligand of methoxy and methyl groups is disclosed in co-pending application Ser. No. 08/779,640, filed Jan. 7, 1997, entitled "Precursor with (Methoxy)(methyl)silylolefin Ligands to Deposit Cu and Method for Same", invented by Senzaki et al., and assigned to the same assignee as the instant patent. The disclosed precursor permits either one or two methoxy groups to be bonded to the silicon atom of the ligand. That is, the precursor can be "fine tuned" using ligands having more methoxy groups than tmvs, but less than tmovs are provided. The oxygen atoms in the methoxy groups contribute electrons to the Cu atoms, to strengthen the Cu-olefin bond, and so, prevent the premature decomposition of the precursor in storage, or as the precursor is heated for the application of Cu to an IC surface. However, only hydrocarbon groups of one carbon atom, $CH_3$ (methyl) and $OCH_3$ (methoxy), are disclosed.

A Cu precursor comprising a ligand of alkyl and alkyl groups is disclosed in U.S. Pat. No. 5,767,301, entitled "Precursor with (Alkyloxy)(Alkyl)silylolefin Ligands to Deposit Copper", invented by Senzaki et al. The disclosed precursor describes alkyl groups bonded to the silicon atom of the ligand with alkoxyl groups. However, the search continues for even more effective copper precursors.

Wei—Wei Zhuang et al., in co-pending patent application Ser No. 09/210,099, entitled "Substituted Phenylethylene Precursor and Synthesis Method", filed Dec. 10, 1998, disclose a volatile copper precursor compound comprising $Cu^{+1}$(hexafluoroacetylacetonate), and a substituted phenylethylene ligand including one phenyl group bonded to a first carbon atom. The remaining bond to the first carbon atom is selected from a first group consisting of $C_1$ to $C_6$ alkyl, $C_1$ to $C_6$ haloalkyl, $C_1$ to $C_6$ phenyl, and $C_1$ to $C_6$ alkoxyl. A second carbon atom includes a second and third bond. The second and third bonds are selected, independent of each other, from the group consisting of H, $C_1$ to $C_6$ alkyl, $C_1$ to $C_6$ phenyl, and $C_1$ to $C_6$ alkoxyl.

Wei—Wei Zhuang et al., in co-pending patent application Ser. No. 09/215,921, entitled "Substituted Ethylene Precursor and Synthesis Method", filed Dec. 18, 1998, disclose a volatile metal (M) precursor compound for the chemical vapor deposition (CVD) of metal to selected surfaces. The precursor compound comprises $M^{+1}$ (hexafluoroacetylacetonate), and a substituted ethylene ligand with a first carbon atom including a first and second bond. The first and second bonds are selected from groups independent of each other. The first bond is selected from a group consisting of $C_1$ to $C_8$ alkyl, $C_1$ to $C_8$ haloalkyl, and $C_1$ to $C_8$ alkoxyl. The second bond is selected from a group consisting of H, $C_1$ to $C_8$ alkyl, $C_1$ to $C_8$ haloalkyl, and $C_1$ to $C_8$ alkoxyl. A second carbon atom includes a third and fourth bond. The third and fourth bonds are selected, independent of each other, from the group consisting of H, $C_1$ to $C_8$ alkyl, $C_1$ to $C_8$ haloalkyl, and $C_1$ to $C_8$ alkoxyl.

Wei—Wei Zhuang et al., in co-pending application Ser. No. 09/281,722 entitled "Alkene Ligand Precursor and Synthesis Method", filed Mar. 30, 1999, disclose a metal (hfac), alkene ligand precursor. The alkene ligand includes double bonded carbon atoms, with first and second bonds to the first carbon atom, and third and fourth bonds to the second carbon atom. The first, second, third, and fourth bonds are selected from a the group consisting of H, $C_1$ to $C_8$ alkyl, $C_1$ to $C_8$ haloalkyl, and $C_1$ to $C_8$ alkoxyl.

As mentioned by Norman et al. in U.S. Pat. No. 5,085,731 (col. 10, lines 34–49), precursors have been made with allyltrimethylsilane (ATMS) that did not form either a volatile liquid or a solid complex. Norman et al. state that "olefinic molecules which simply contain a silicon group not directly attached to the olefinic double bond do not stabilize $Cu^{+1}$(hfac) as effectively as those in which silicon is directly attached to the double bond." However, Man-Young Park et al., in "Chemical Vapor Deposition of Copper Thin Films with (hexafluoroacetylacetonate)Cu(allyltrimethylsilane)", Electrochemical and Solid-State Letters, 1, 1, 32–33, (1998), claim the fabrication of precursors with the ATMS ligand.

It would be advantageous if a copper precursor was found that effectively deposits copper with low resistivity and good adhesion properties. It would be further advantageous if this precursor was inexpensive to synthesize.

It would be advantageous if a method were found of making a Cu(hfac) precursor stable over a wider range of temperatures, and to provide that the precursor remain in liquid phase during storage.

It would be advantageous if a precursor could be developed where silylolefin groups are not directly attached to olefinic double bonds.

It would be advantageous if a precursor could be developed which encouraged a stable $Cu^{+1}$(hfac) bond without the use of silylolefins directly bonded to olefinic double bonds.

It would be advantageous if a metal precursor could be developed which made use of allyl-derived ligands to stabilize the precursor.

Accordingly, a volatile metal (M) precursor compound for the chemical vapor deposition (CVD) of metal, such as copper, silver, and iridium, to selected surfaces has been provided. The precursor compound comprises $M^{+1}$ (hexafluoroacetylacetonate) and an allyl-derived ligand. The allyl-derived ligand includes a first carbon atom double bonded to a second carbon atom. The first carbon atom has a first bond to a methylene and a second bond to an hydrogen (H) molecule. The second carbon has a third bond to an H molecule and a fourth bond to an H molecule. The methylene has a further bond to a molecule selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, pentafluorobenzene, whereby a stable precursor capable of high metal deposition rates is formed.

To improve the stability of the precursor an additive is sometimes added to create a precursor blend. Then, the precursor blend further comprises:

less than approximately 10% substituted allyltrimethylsilane, as measured by weight ratio of the precursor compound, to facilitate a stable liquid phase precursor. Alternately, when some other allyl-derived ligand, besides ATMS, is used to form the precursor, that same allyl-derived ligand is used as the additive.

A method for synthesizing a copper(hfac) allyl-derived precursor has also been provided. Similar processes could be used to fabricate silver or iridium precursors. The method steps for forming Cu(hfac)(ATMS) are:

a) forming a uniformly mixed solution of 12 grams (g) $Cu_2O$ proportionally to 40 milliliters (ml) of dichloromethane solvent;

b) introducing 16.15 g of ATMS proportionally to the solution of Step a), and forming a uniformly mixed solution;

c) introducing 20 ml of hexafluoroacetylacetone proportionally to the solution of Step b), and forming a uniformly mixed solution;

d) filtering the solution to remove solid material in the solution, whereby excess $Cu_2O$ is removed;

e) stripping the solution of dichloromethane solvent; and f) filtering the solution to remove solid material and crystallized compounds, whereby a liquid phase stable precursor is formed.

Specifically, Step a) includes the $Cu_2O$, in proportion, of 0.084 mol, in which Step b) includes ATMS, in proportion, of 0.141 mol, and Step c) includes the hfac, in proportion, of 0.141 mol.

DETAILED DESCRIPTION OF THE PREFERRED EMBODIMENT

The allyl-derived ligand copper precursor, disclosed below, is inexpensive to synthesize. Compared to trimethylvinylsilane, which costs approximately $180 per 100 g, allyltrimethylsilane is less inexpensive, at approximately $136 per 100 g. The precursor is stable at room temperature for easy storage and handling. Despite retaining its liquid phase at room temperature, it is highly volatile at higher temperatures. Therefore, no decomposition occurs in the CVD liquid delivery line and vaporizer, which requires precursor stability at 90 degrees C, under vacuum, for four minutes. Further, the precursor has excellent adhesion to metal and metal nitride substrates, such as W, Ti, TiN, Ta, TaN, Al, Pt, WN, and similar barrier materials. The copper deposited with precursor has low resistivity (<1.9 $\mu\Omega$·cm), high electromigration resistance, and excellent conformality to severe surface morphology.

Figure 1:
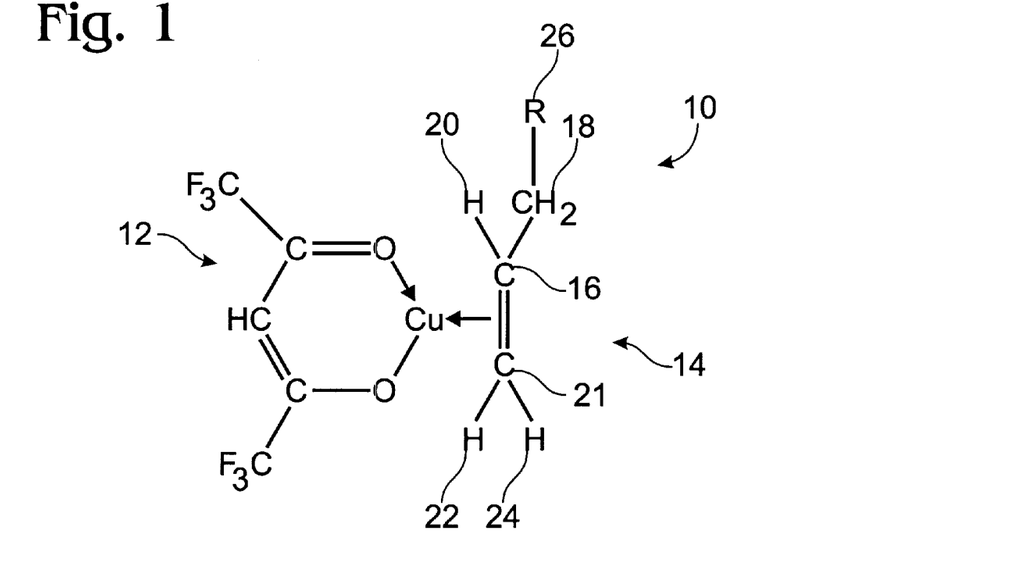
FIG. 1 is a schematic representation of the present invention precursor with a allyl-derived ligand.

FIG. 1 is a schematic representation of the present invention precursor with a allyl-derived ligand. A volatile metal (M) precursor 10 compound for the chemical vapor deposition (CVD) of metal to selected surfaces is shown. Precursor compound 10 comprises $M^{+1}$ (hexafluoroacetylacetonate) 12 and an allyl-derived ligand 14. The precursor deposition metal (M) is selected from the group consisting of copper, silver, and iridium.

First carbon atom 16 has a first bond to methylene 18 and a second bond to a hydrogen atom (H) 20. A second carbon 21, which is double bonded to first carbon atom 16, has a third bond to an H 22 and a fourth bond to an H 24. Methylene 18 has a fifth bond selected from the group 26, represented as "R". Group 26 consists of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene. A stable precursor capable of high metal deposition rates is formed using the above-mentioned allyl-derived ligands 14.

In some aspects of the invention, allyl-derived precursor compound 10 further includes an additive (see FIGS. 3 and 4) to create a precursor blend. The blend facilitates a stable liquid phase precursor. The precursor blend further comprises less than approximately 10% allyl-derived ligand, as measured by weight ratio of the precursor compound 10, to facilitate a stable liquid phase precursor.

Figure 2:
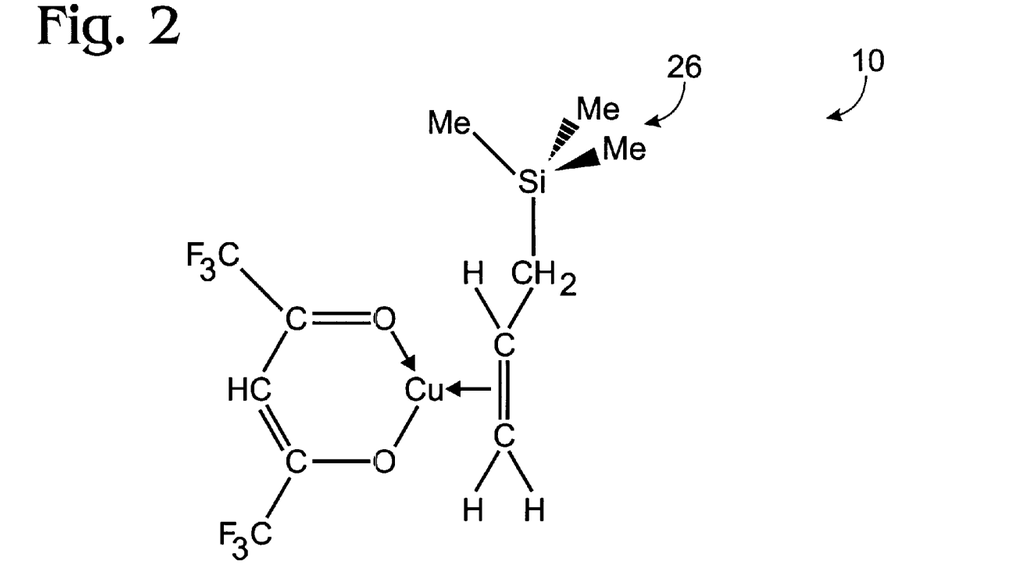
FIG. 2 illustrates an embodiment of the invention where the fifth bond to methylene, selected from the above-mentioned group, is trimethylsilane, whereby an allyltrimethylsilane (ATMS) ligand is formed.

FIG. 2 illustrates an embodiment of the invention where the fifth bond to methylene, selected from above-mentioned group 26, is trimethylsilane. Allyltrimethylsilane (ATMS) ligand 14 forms a M(hfac)(ATMS) precursor 10. ATMS Precursor compound 10 further includes an additive (see FIGS. 3 and 4) to create a precursor blend. The blend facilitates a stable liquid phase precursor. The precursor blend further comprises less than approximately 10% allyltrimethylsilane, as measured by weight ratio of the precursor compound 10, to facilitate a stable liquid phase M(hfac)ATMS precursor 10.

Alternately, the volatile metal (M) precursor compound 10, described above and shown in FIGS. 1 and 2 is represented with the following structural formula:

(H₂C=CHCH₂R)M⁺¹(hfac)

in which R is selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene, whereby a precursor is formed from an allyl-derived ligand.

Figure 3:
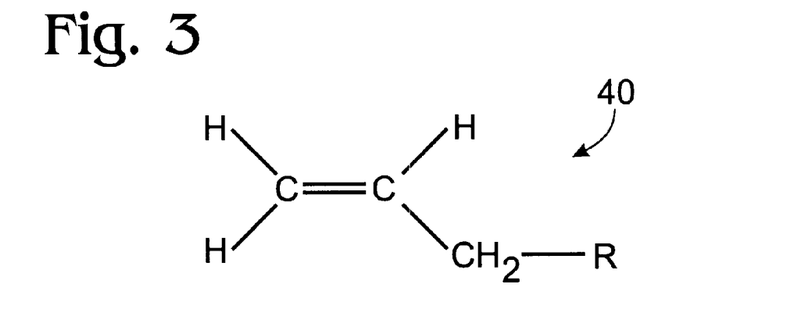
FIG. 3 is a schematic representation of an allyl-derived ligand additive.

FIG. 3 is a schematic representation of an allyl-derived ligand additive 40. In some aspects of the invention, the metal precursor compound includes an allyl-derived additive to create a metal precursor blend. The allyl-derived additive having the following structural formula:

H₂C=CHCH₂R.

The R bond is selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene. The additive permits the precursor to be further stabilized in a liquid phase. The allyl-derived ligand selected to form the precursor is the same allyl-derived additive used to from the precursor blend. Typically, the additive is less than approximately 10% by weight ratio of the precursor blend. In one embodiment, the additive is approximately 4.7% by weight ratio of the precursor blend.

Figure 4:
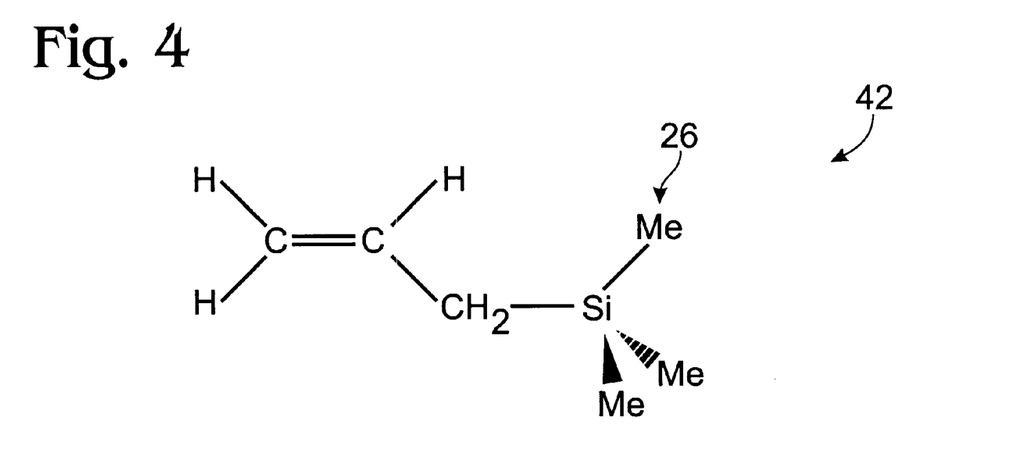
FIG. 4 is a schematic representation of a preferred ATMS ligand additive.

In some aspects of the invention, the metal is copper and R is trimethylsilane, so that an ATMS ligand precursor is formed. The metal precursor compound also includes an ATMS ligand additive to create a metal precursor blend. The allyl-derived additive having the following structural formula:

H₂C=CHCH₂Si(CH₃)₃.

The ATMS additive permits the precursor to be further stabilized in a liquid phase. Typically, the additive is less than approximately 10% by weight ratio of the precursor blend. In one embodiment, the additive is approximately 4.7% by weight ratio of the precursor blend. FIG. 4 is a schematic representation of a preferred ATMS ligand additive 42.

Figure 5:
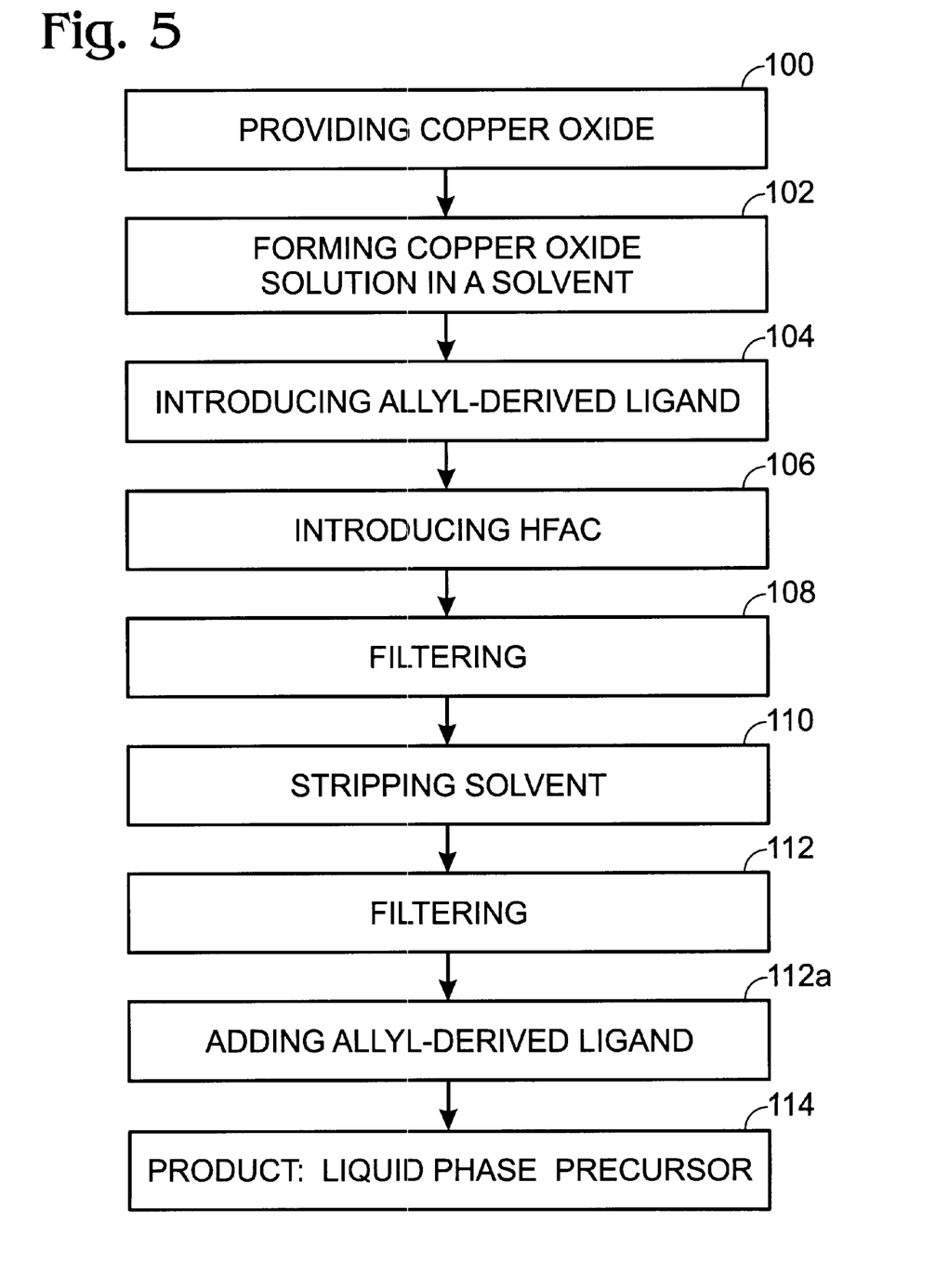
FIG. 5 is a flowchart illustrating steps in a method for synthesizing a copper(hfac) allyl-derived precursor.

FIG. 5 is a flowchart illustrating steps in a method for synthesizing a copper(hfac) allyl-derived precursor. The synthesis method is generally applicable to the fabrication of silver and iridium precursors. Step 100 provides copper oxide (Cu₂O). Step 102 forms a uniformly mixed solution of Cu₂O in a solvent. Specifically, Step 102 includes using a solvent selected from the group consisting of dichloromethane and tetrahydrofuran (THF). Step 104 introduces an allyl-derived ligand to the solution of Step 102, and forming a uniformly mixed solution. Preferably, Step 104 includes the allyl-derived ligand being trimethylsilane, whereby an allyltrimethylsilane (ATMS) ligand is formed. Step 106 introduces hexafluoroacetylacetone (hfac) to the solution of Step 104, and forms a uniformly mixed solution. Step 108 filters the solution to remove solid materials, whereby any excess Cu₂O is removed. Typically, Step 108 includes removing solid material larger than approximately 10 microns. Celite is used to filter the solution. Step 110 removes the solvent from the solution. Step 112 filters to remove the solid material. Step 112 includes filtering solid material having a size greater than approximately 1 micron. Step 114 is a product, where a liquid phase precursor is formed.

Specifically, Step 102 includes the Cu₂O being, in proportion, 0.084 mol. Step 104 includes the allyl-derived ligand being, in proportion, 0.141 mol, and Step 106 includes the hfac being, in proportion, 0.141 mol.

In some aspects of the invention, a further step follows Step 112. Step 112a adds less than approximately 10%, by weight ratio, of the allyl-derived ligand used in Step 104 to the solution, whereby the liquid phase stability of the precursor is improved. Typically, Step 112a includes adding approximately 4.7% allyl-derived ligand.

Figure 6:
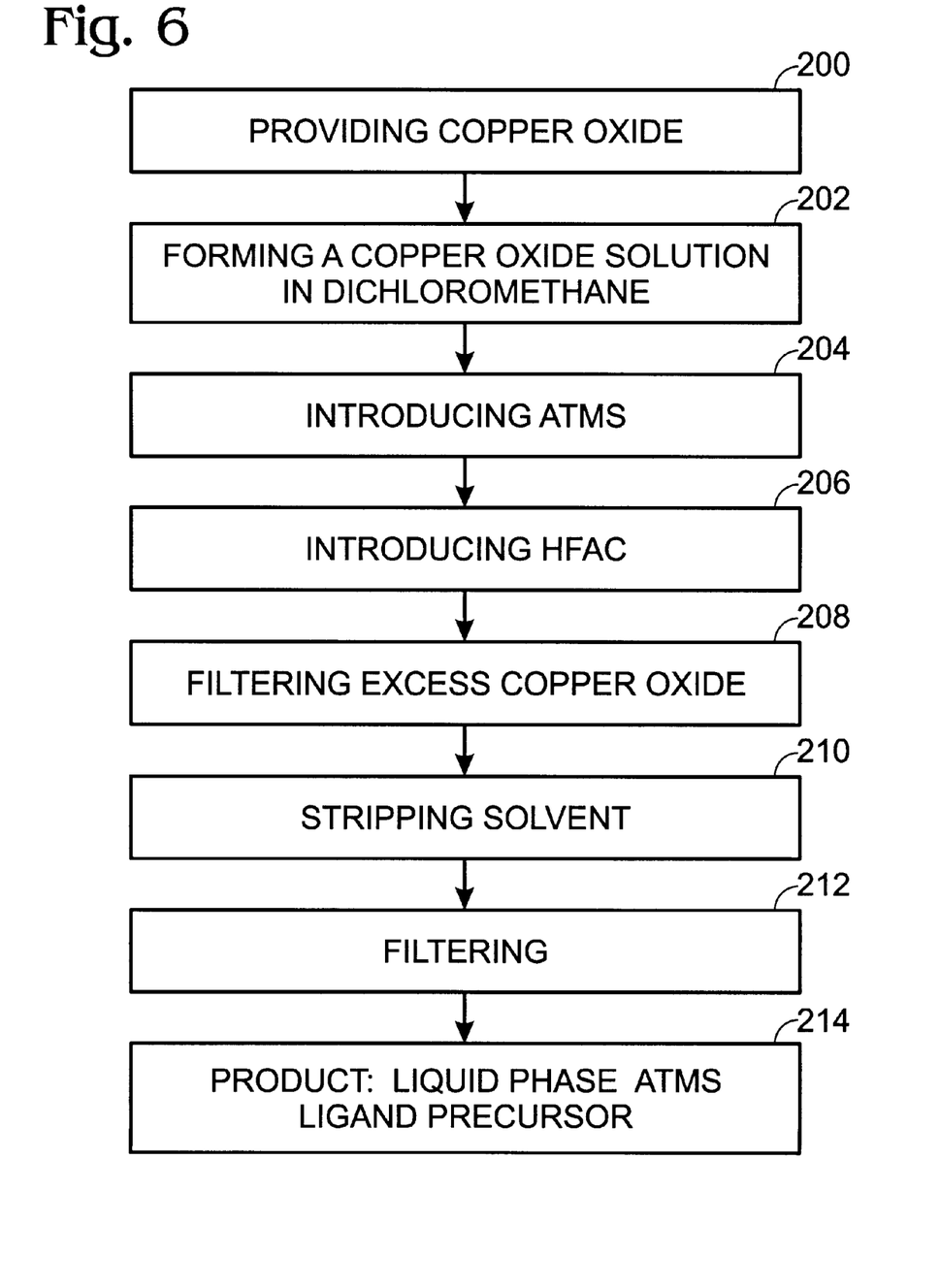
FIG. 6 is a flowchart illustrating a method for synthesizing a copper(hfac) allyltrimethylsilane (ATMS) precursor.

FIG. 6 is a flowchart illustrating a method for synthesizing a copper(hfac) allyltrimethylsilane (ATMS) precursor. The procedure is generally applicable to the fabrication of silver and Ir ATMS precursors. Step 200 provided copper oxide. Step 202 forms a uniformly mixed solution of 12 grams (g) Cu₂O proportionally to 40 milliliters (ml) of dichloromethane solvent. Step 204 introduces 16.15 g of ATMS proportionally to the solution of Step 202, and forming a uniformly mixed solution. Step 206 introduces 20 ml of hexafluoroacetylacetone proportionally to the solution of Step 204, and forming a uniformly mixed solution. Step 208 filters the solution to remove solid material in the solution, whereby excess Cu₂O is removed. Step 210 strips the solution of dichloromethane solvent. Step 212 filters the solution to remove solid material and crystallized compounds. Step 214 is a product, where a liquid phase stable precursor is formed.

Specifically, Step 202 includes the Cu₂O, in proportion, of 0.084 mol, Step 204 includes ATMS, in proportion, of 0.141 mol, and Step 206 includes the hfac, in proportion, of 0.141 mol.

In some aspects of the invention, a further step follows Step 208 and precedes Step 212. Step 210a heats the solution to approximately 35 degrees C to aid in the stripping of solvent from the solution.

All manipulations were carried out in an air-free dry glovebox or by using standard Schlenk techniques. Solvents were purified before synthesis. Dichloromethane was refluxed and distilled over calcium hydride under an atmosphere of nitrogen prior to use. Allyltrimethylsilane and 1,1,1,5,5,5-hexafluoroacetylacetone were purchased from Aldrich and Strem respectively, and used directly without any purification. Although the synthesis of Cu(hfac)(ATMS) is described below, the procedures are generally applicable to the class of allyl-derived ligands.

The synthesis procedure of organometallic copper(I) complexes was firstly described by Doyle in U.S. Pat. No. 4,385,005, in which copper monoxide reacted with unsaturated organic hydrocarbon and 1,1,1,5,5,5-hexafluoroacetylacetone, in dichloromethane or THF. The reaction is described by the following equation:

$$Cu_2O + 2(CF_3)C(O)CH_2C(O)(CF_3) + 2L \xrightarrow{CH_2Cl_2 \text{ or THF}} 2\,Cu(hfac)(L)$$

where L is unsaturated organic hydrocarbon ligand.

According to the synthesis procedure above, the synthesis of (ATMS)Cu(hfac) yields a product which is not stable at room temperature for long periods of time. To solve this problem, approximately 5% allyltrimethylsilane (by product weight) was added into the product for the compound stabilization. After one month, no solid precipitation was observed in the stabilized product.

In the synthesis of (atms)Cu(hfac), $Cu_2O$ (12 g, 0.084 mol) was added into a 100 ml round bottom flask equipped with $CH_2Cl_2$ (40 mL) and a stirring bar. To this $Cu_{20}$ dichloromethane solution, allyltrimethylsilane (16.15 g, 0.141 mol) was added and stirred at room temperature for five minutes. Then 1,1,1,5,5,5-hexafluoroacetylacetone (20 mL, 0.141 mol) was introduced into this red color solution, while stirring. After 2 minutes, the solution color gradually changed to green. The green solution was continually stirred for another 10 minutes, and then filtered through celite (the filter size is 10–25 $\mu$m). The green filtrate was stripped under vacuum for two hours and then heated to 35° C. under vacuum for another half-hour stripping. This filtering and stripping process produced a green liquid organometallic copper compound, which was then filtered through a fine filter (1 $\mu$m) to give 41.67 gram product (yield: 76.63% based on hfac, and the theoretical yield based on hfac is 54.38 gram.). To stabilize the product, two experiments were carried out. In the first one, allyltrimethylsilane (0.067 g) was introduced into the product (3.132 g). This produced a solution with 2.1% extra allyltrimethylsilane in (atms)Cu(I) (hfac). In the second experiment, allyltrimethylsilane (0.170 g) was introduced into the product (3.800 g). This produced a solution with 4.3% extra allyltrimethylsilane in (atms)Cu (I)(hfac). After one month, little reddish precipitate was seen in the first experiment, but no solid precipitates were observed in the second experiment. Therefore, the new liquid organometallic compound is stabilized by the addition of approximately 5% extra allyltrimethylsilane.

The NMR structural analysis was carried out on a 300 MHz NMR instrument. The results were as follows: $^1$H NMR ($C_6D_6$) $\delta$–2.10 (s, 9, $CH_2$=CHCH$_2$Si(CH$_3$)$_3$), 1.02 (d, 2, $CH_2$=CHCH$_2$Si(CH$_3$)$_3$), 3.61 (d, 1, $J_{HH}$=4.5 Hz, $CH_2$=CHCH$_2$Si(CH$_3$)$_3$ (trans to $CH_2$)), 3.65 (s, 1, $CH_2$=CHCH$_2$Si(CH$_3$)$_3$ (cis to $CH_2$)), 4.71 (multi., 1, $J_{HH}$= 7.8 Hz, $CH_2$=CHCH$_2$Si(CH$_3$)$_3$), 6.20 (s, 1, ($CF_3$C(O)CHC (O)CF$_3$).

The results of copper metal thin film deposition via CVD using (atms)Cu(I)(hfac) liquid precursor were very good. The copper thin films have shown good adhesion to metal and metal nitride substrates, low resistivity (1.8 $\mu\Omega$·cm), and also very good reproducibility. The precursor is very volatile, and thus high deposition rate has been achieved.

A new and improved copper precursor, and synthesis method for the copper precursor, has been disclosed above. The precursor, especially the ATMS ligand precursor, is stable a low (room) temperatures, and sufficiently volatile at higher temperatures. Copper deposited with the precursor has low resistivity and high adhesive characteristics. Finally, the precursor is inexpensive to make. A synthesis method has been disclosed which produces a high yield of the above-described precursor. Other variations and embodiments will occur to those skilled in the art.

What is claimed is:

1. A volatile metal (M) precursor compound for the chemical vapor deposition (CVD) of metal to selected surfaces, the precursor compound comprising:

$M^{+1}$(hexafluoroacetylacetonate); and an allyl-derived ligand including a first carbon atom having a first bond to a methylene and a second bond to an H, and a second carbon double bonded to said first carbon atom, having a third bond to an H and a fourth bond to an H, and in which said methylene has a fifth bond selected from the group consisting of alkyl, phenyl, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene, whereby a stable precursor capable of high metal deposition rates is formed.

2. A volatile metal (M) precursor compound for the chemical vapor deposition (CVD) of metal to selected surfaces, wherein the compound includes an additive to create a precursor blend, the precursor compound comprising:

$M^{+1}$(hexafluoroacetylacetonate):

an allyl-derived ligand including a first carbon atom having a first bond to a methylene and a second bond to an H, and a second carbon double bonded to said first carbon atom, having a third bond to an H and a fourth bond to an H, and in which said methylene has a fifth bond, in which the fifth bond to said methylene is trimethylsilane to form a M(hfac)(ATMS) precursor; and in which the precursor blend further comprises:

less than approximately 10% allyltrimethylsilane, as measured by weight ratio of the precursor compound, to facilitate a stable liquid phase precursor.

3. A volatile metal (M) precursor compound for the chemical vapor deposition (CVD) of metal to selected surfaces, wherein the precursor deposition metal is selected from the group consisting of silver and iridium, the precursor compound comprising:

$M^{+1}$(hexafluoroacetylacetonate); and an allyl-derived ligand including a first carbon atom having a first bond to a methylene and a second bond to an H, and a second carbon double bonded to said first carbon atom, having a third bond to an H and a fourth bond to an H, and in which said methylene has a fifth bond selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene, whereby a stable precursor capable of high metal deposition rates is formed.

4. A volatile metal (M) precursor compound for the chemical vapor deposition (CVD) of metal to selected surfaces, wherein the compound includes an additive to create a precursor blend, the precursor compound comprising:

$M^{+1}$(hexafluoroacetylacetonate);

an allyl-derived ligand including a first carbon atom having a first bond to a methylene and a second bond to an H, and a second carbon double bonded to said first carbon atom, having a third bond to an H and a fourth bond to an H, and in which said methylene has a fifth bond selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene; and in which the precursor blend further comprises:

less than approximately 10% allyl-derived ligand, as measured by weight ratio of the precursor compound, to facilitate a stable liquid phase precursor.

5. A volatile metal (M) precursor compound for applying chemical vapor deposition (CVD) M to selected surfaces, the precursor compound having the following structural formula:

(H₂C=CHCH₂R)M⁺¹(hfac)

in which R is selected from the group consisting of alkyl, phenyl, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene, whereby a precursor is formed from an allyl-derived ligand.

6. A volatile metal (M) precursor compound for applying chemical vapor deposition (CVD) M to selected surfaces, wherein the metal is copper the precursor compound having the following structural formula:

(H₂C=CHCH₂R)M⁺¹(hfac)

in which R is trimethylsilane, so that an ATMS ligand precursor is formed including an ATMS ligand additive to create a metal precursor blend, the allyl-derived additive having the following structural formula:

H₂C=CHCH₂Si(CH₃)₃ in which the additive is approximately 4.7% by weight ratio of the precursor blend.

7. A volatile metal (M) precursor compound for applying chemical vapor deposition (CVD) M to selected surfaces, the precursor compound having the following structural formula:

(H₂C=CHCH₂R)M⁺¹(hfac)

in which R is selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene; and in which the compound includes an allyl-derived additive to create a metal precursor blend, the allyl-derived additive having the following structural formula:

H₂C=CHCH₂R in which the R bond is selected from the group consisting of alkyl, phenyl, trialkylsilane, trialkoxylsilane, halodialkylsilane, dihaloalkylsilane, trihalosilane, triphenylsilane, alkoxyl, halogen, chloroformate, cynanide, cycloalkyl, cycloalkylamine, alkyl ether, isocyanate, and pentafluorobenzene, whereby the precursor is further stabilized in a liquid phase.

8. The metal precursor as in claim 7 in which the additive is less than approximately 10% by weight ratio of the precursor blend.

9. The metal precursor as in claim 7 in which the allyl-derived ligand selected to form the precursor is the same allyl-derived additive used to from the precursor blend.

10. A method for synthesizing a copper(hfac) allyl-derived precursor comprising the steps of:

a) forming a uniformly mixed solution of Cu₂O in a solvent;

b) introducing an allyl-derived ligand to the solution of Step a), and forming a uniformly mixed solution;

c) introducing hexafluoroacetylacetone (hfac) to the solution of Step b), and forming a uniformly mixed solution;

d) filtering the solution to remove solid materials, whereby any excess Cu₂O is removed;

e) removing the solvent from the solution; and f) filtering to remove the solid material, whereby a liquid phase precursor is formed.

11. A method as in claim 10 in which Step b) includes the allyl-derived ligand being trimethylsilane, whereby an allyl-trimethylsilane (ATMS) ligand is formed.

12. A method as in claim 10 in which Step a) includes the Cu₂O being, in proportion, 0.084 mol, in which Step b) includes the allyl-derived ligand being, in proportion, 0.141 mol, and in which Step c) includes the hfac being, in proportion, 0.141 mol.

13. A method as in claim 10 in which Step d) includes removing solid material larger than approximately 10 microns.

14. A method as in claim 13 in which Step d) includes using celite to filter the solution.

15. A method as in claim 10 in which Step a) includes using a solvent selected from the group consisting of dichloromethane and tetrahydrofuran (THF).

16. A method as in claim 10 in which Step f) includes filtering solid material having a size greater than approximately 1 micron.

17. A method as in claim 10 comprising a further step, following Step f), of:

g) adding less than approximately 10%, by weight ratio, of the allyl-derived ligand used in Step b) to the solution, whereby the liquid phase stability of the precursor is improved.

18. A method as in claim 17 in which Step g) includes adding approximately 4.7% allyl-derived ligand.

19. A method for synthesizing a copper(hfac) allyltrimethylsilane (ATMS) precursor comprising the steps of:

a) forming a uniformly mixed solution of 12 grams (g) Cu₂O proportionally to 40 milliliters (ml) of dichloromethane solvent;

b) introducing 16.15 g of ATMS proportionally to the solution of Step a), and forming a uniformly mixed solution;

c) introducing 20 ml of hexafluoroacetylacetone proportionally to the solution of Step b), and forming a uniformly mixed solution;

d) filtering the solution to remove solid material in the solution, whereby excess Cu₂O is removed;

e) stripping the solution of dichloromethane solvent; and f) filtering the solution to remove solid material and crystallized compounds, whereby a liquid phase stable precursor is formed.

20. A method as in claim 19 in which Step a) includes the Cu₂O, in proportion, of 0.084 mol, in which Step b) includes ATMS, in proportion, of 0.141 mol, and in which Step c) includes the hfac, in proportion, of 0.141 mol.

21. A method as in claim 19 including a further step, following Step d), and preceding Step f), of:

e₁) heating the solution to approximately 35 degrees C to aid in the stripping of solvent from the solution.

* * * * *